(12) United States Patent
Ichihara

(10) Patent No.: US 8,761,225 B2
(45) Date of Patent: Jun. 24, 2014

(54) LASER APPARATUS AND METHOD OF CONTROLLING THE LASER APPARATUS

(71) Applicant: Canon Kabushiki Kaisha, Tokyo (JP)

(72) Inventor: Shigeru Ichihara, Tokyo (JP)

(73) Assignee: Canon Kabushiki Kaisha, Tokyo (JP)

( * ) Notice: Subject to any disclaimer, the term of this patent is extended or adjusted under 35 U.S.C. 154(b) by 0 days.

(21) Appl. No.: 13/672,349

(22) Filed: Nov. 8, 2012

(65) Prior Publication Data

US 2013/0070802 A1  Mar. 21, 2013

Related U.S. Application Data

(63) Continuation of application No. PCT/JP2012/065662, filed on Jun. 19, 2012.

(30) Foreign Application Priority Data

Jun. 20, 2011  (JP) .................... 2011-136236

(51) Int. Cl.
*H01S 3/091* (2006.01)
(52) U.S. Cl.
USPC ...... 372/70; 372/41; 372/29.011; 372/29.015
(58) Field of Classification Search
USPC ............... 372/70, 41, 29.011, 29.015
See application file for complete search history.

(56) References Cited

U.S. PATENT DOCUMENTS

| | | | |
|---|---|---|---|
| 5,481,556 A * | 1/1996 | Daikuzono | 372/34 |
| 6,193,711 B1 * | 2/2001 | Connors et al. | 606/12 |
| 6,330,258 B1 | 12/2001 | Kawamura | |

FOREIGN PATENT DOCUMENTS

| | | | | |
|---|---|---|---|---|
| JP | 57-106189 A | 7/1982 | | |
| JP | 2-119853 A | 5/1990 | | |
| JP | 8-195521 A | 7/1996 | | |
| JP | 2542821 B2 | 7/1996 | | |
| JP | 2-542821 B2 | 10/1996 | | |
| JP | 10-163550 A | 6/1998 | | |
| JP | 10163550 A * | 6/1998 | ............. | H01S 3/092 |
| JP | 2000-208841 A | 7/2000 | | |

OTHER PUBLICATIONS

Manohar, S., et al., "Region-of-Interest breast studies using the Twente Photoacoustic Mammoscope (RAM)," Proc. of SPIE, vol. 6437, pp. 643702-1 to 643702-9 (2007).
Written Opinion of the International Searching Authority issued in International Application No. PCT/JP2012/065662.
Manohar, S., et al., "Region-of-Interest breast studies using the Twente Photoacoustic Mammoscope (PAM)," Proc. of SPIE, vol. 6437, pp. 643702-1 to 643702-9 (2007).

* cited by examiner

*Primary Examiner* — Kinam Park
(74) *Attorney, Agent, or Firm* — Fitzpatrick, Cella, Harper & Scinto

(57) ABSTRACT

Disclosed is a method of controlling a laser apparatus, which has a laser light irradiation unit, an excitation unit including a flash lamp, a laser light shielding unit, and a control unit configured to control light shielding by the light shielding unit and release of the light shielding and control setting conditions of the flash lamp. The control unit performs a process of blocking the laser light by the light shielding unit when irradiation of the laser light is stopped, then performs a process of controlling the setting condition so that consumption of the flash lamp is reduced, performs, when the irradiation is restarted, a process of controlling the setting conditions so that the laser light is stably irradiated, and then performs a process of releasing the light shielding.

14 Claims, 11 Drawing Sheets

LASER APPARATUS AND METHOD OF CONTROLLING THE LASER APPARATUS

BACKGROUND OF THE INVENTION

1. Field of the Invention

The present invention relates to a laser apparatus and a method of controlling the laser apparatus.

2. Description of the Related Art

Realization of a high output of a laser instrument has progressed over time. Particularly, a solid laser (typified by a Nd:YAG laser and so on using a laser medium obtained by adding neodymium (Nd) to $Y_3Al_5O_{12}$ crystal as a base material) is suitable for high energy applications. A noble-gas flash lamp and a semiconductor laser (LD) are used as an excitation source for a solid laser, and the noble-gas flash lamp has the advantages that it is inexpensive and that energy output per pulse can be increased. Thus, the noble-gas flash lamp is widely used for industrial applications such as a laser light machine and a laser annealing apparatus.

Recently, the development of photoacoustic measurement apparatus for medical use using laser light has progressed (NPL 1, below). In such an apparatus, a diagnosis of the presence of a tumor in the breast using the photoacoustic effect has been attempted. The photoacoustic measurement apparatus is a measurement apparatus which irradiates a portion of tissue (a "measured portion") with a nanosecond pulse laser to receive an ultrasound wave (photoacoustic wave) generated in the measured portion, and, thus, to analyze a received signal, whereby an image is obtained. Especially, in order to obtain a photoacoustic signal from a relatively deep biological portion, laser light of high energy output per pulse is required, and a lamp excitation solid laser is suitably used.

However, since the emission spectrum of a flash lamp is as wide as from the ultraviolet region to the infrared region, the flash lamp is less consistent with an absorption spectrum of a laser medium. Thus, a thermal load is applied to the laser medium, and there is the disadvantage that beam quality deteriorates due to the thermal lens effect, the thermal birefringence effect, and so on. Especially, the output energy at the initial stage of rising of the laser oscillation is unstable until the laser medium reaches thermal equilibrium. Thus, since the laser oscillation output gradually changes, a problem occurs in processing and so on.

To respond to the above problem, there is disclosed a method of measuring the laser output for each pulse to control a lamp current supplied from a power supply to a flash lamp so that each pulse energy is constant, and, thus, to obtain a stable output (PTL 1, below).

Flash lamps have different characteristics from each other. As the flash lamp is used, the emission intensity is reduced, and the flash lamp eventually needs to be exchanged. The consumption of the flash lamp strongly affects the convenience of a lamp excitation solid laser. To respond to this problem, there is disclosed a method of detecting the laser output as needed by a photodetection element, then, when the lamp current value is more than a predetermined upper limit value or lower limit value, displaying the fact, and indicating the need to exchange the flash lamp by the display (PTL 2, below).

In the laser apparatus using the lamp excitation solid laser, it is very important to control a lamp setting value to enhance the convenience.

PTL 1: Japanese Patent No. 2542821
PTL 2: Japanese Patent Application Laid-Open No. 8-195521
NPL 1: S. Manohar et al., *Proc. of SPIE*, vol. 6437, 643702-1

SUMMARY OF THE INVENTION

Although a flash lamp used in a lamp excitation solid laser depends on the internal constitution of a laser head and lamp setting conditions at the time of irradiation, the life of the flash lamp may be taken as being approximately ten million shots. The flash lamp has an individual specificity in the length of its life, and at times the life is approximately several million shots even in the flash lamp having the same specification. Although the consumption of the flash lamp in the lamp excitation solid laser is inevitable, when convenience of the laser apparatus is considered, it is very important to increase the exchange cycle of the flash lamp.

When the flash lamp is turned off at the time of light shielding, the consumption of the flash lamp is reduced. However, it takes a long time for a laser medium to reach a thermal equilibrium state when irradiation is restarted, so that it takes a long time to stabilize the output, and thus convenience is lost. Further, the light emission of the flash light when not in use (corresponding to the warm-up time) leads to the lamp consumption. Meanwhile, when the output stability at the time when the laser light is irradiated is emphasized and the laser oscillation output at the time when the laser light is blocked is maintained similar to that at the time when the laser light is irradiated, lamp consumption also occurs due to unnecessary irradiation of the flash lamp. Namely, a lamp control method of enhancing the output stability at the time when the laser light is irradiated and, at the same time, reducing the lamp consumption at the time of light shielding to stably utilize the lamp excitation solid laser for a long time of period is very important.

However, although PTL 1 as a conventional example discloses a method of performing lamp control in view of satisfying the output stability for each pulse, the contents regarding the reduction of the lamp consumption are not included therein. Although PTL 2 discloses a method of performing laser output measurement and controlling the lamp current in view of indicating the exchange of the flash lamp based on the lamp consumption, this method is not a control method in view of extending the life of the flash lamp. In the conventional examples, the output stability at the time of irradiation and the reduction of the lamp consumption at the time of light shielding cannot be satisfied simultaneously.

The simultaneous realization of the output stability and the reduction of the lamp consumption become significant problems in a laser apparatus for medical application, particularly a laser apparatus for diagnostic purposes, rather than industrial application such as processing and annealing conventionally often used as the application of a high-output lamp excitation solid laser. In medical diagnostic equipment, it is supposed to perform remeasurement according to a diagnosis result and to repeat measurement according to a diagnosis protocol. Moreover, since the measurement conditions are often changed according to the condition of a subject, the use state is less likely to be standardized, as compared with in an industrial application. Consequently, the time when the laser apparatus is not used may be longer than the time when the laser apparatus is used, and this is very inefficient in terms of utilizing the flash lamp.

In a photoacoustic measurement apparatus for medical diagnosis, measurement time and method and so on are different according to the state of a subject and a condition of a portion to be diagnosed. When the breast is examined for detecting (measuring) a tumor, as well as measuring both breasts, a measurement direction is changed, and measurement and light shielding are repeated according to the usage of the photoacoustic measurement apparatus. The measurement direction is a representation based on a photographing method in an X-ray mammography. The measurement direction includes a Cranio-Caudal (CC) direction, a Medio-Lateral-Oblique (MLO) direction, and a Medial-Lateral (ML) direction. Since the photoacoustic measurement is noninvasive (less-invasive) measurement, it has such characteristics as to enable to perform repeated measurement. Thus, this problem is important to prevent limitation of such a measurement method that laser light irradiation and light shielding are repeated randomly.

In view of the above problems, the present invention provides a laser apparatus, which simultaneously satisfies the laser stability at the time when a laser light is irradiated and the reduction of consumption of a flash lamp at the time when the laser light is blocked, and a method of controlling the laser apparatus.

The present invention employs the following configuration. A method of controlling a laser apparatus has an irradiation unit configured to irradiate a laser light to an irradiated object, an excitation unit configured to excite the irradiation unit by emission of a flash lamp, a light-shielding unit configured to block the laser light irradiated from the irradiation unit, and a control unit configured to control light shielding by the light-shielding unit and release of light shielding and control setting conditions associated with the emission of the flash lamp. The control unit performs, when the irradiation with the laser light from the irradiation unit to the irradiated object is stopped, a process of blocking the laser light by the light-shielding unit, then performing a consumption reduction start process of controlling the setting condition so that the consumption of the flash lamp is reduced, and perform, when the irradiation with the laser light from the irradiation unit to the irradiated object is restarted, a consumption reduction stop process of controlling the setting condition so that the laser light is stably irradiated by the irradiation unit, then performing a process of releasing the light shielding by the light-shielding unit.

The present invention also employs the following configuration. A laser apparatus includes: an irradiation unit configured to irradiate a laser light to an irradiated object; an excitation unit configured to excite the irradiation unit by emission of a flash lamp; a light-shielding unit configured to block the laser light irradiated from the irradiation unit; and a control unit configured to control light shielding by the light-shielding unit and release of light shielding and control setting conditions associated with the emission of the flash lamp, wherein when the irradiation with the laser light from the irradiation unit to the irradiated object is stopped, the control unit blocks the laser light by the light-shielding unit, then controls the setting condition so that the consumption of the flash lamp is reduced; and when the irradiation with the laser light from the irradiation unit to the irradiated object is restarted, the control unit controls the setting condition so that the laser light is stably irradiated by the irradiation unit, and then releases the light shielding by the light-shielding unit.

The present invention can provide a laser apparatus, which simultaneously satisfies the laser stability at the time when a laser light is irradiated and the reduction of consumption of a flash lamp at the time when the laser light is blocked, and a method of controlling the laser apparatus.

Further features of the present invention will become apparent from the following description of exemplary embodiments with reference to the attached drawings.

DESCRIPTION OF THE EMBODIMENTS

Hereinafter, embodiments of the present invention will be described.

Figure 1:
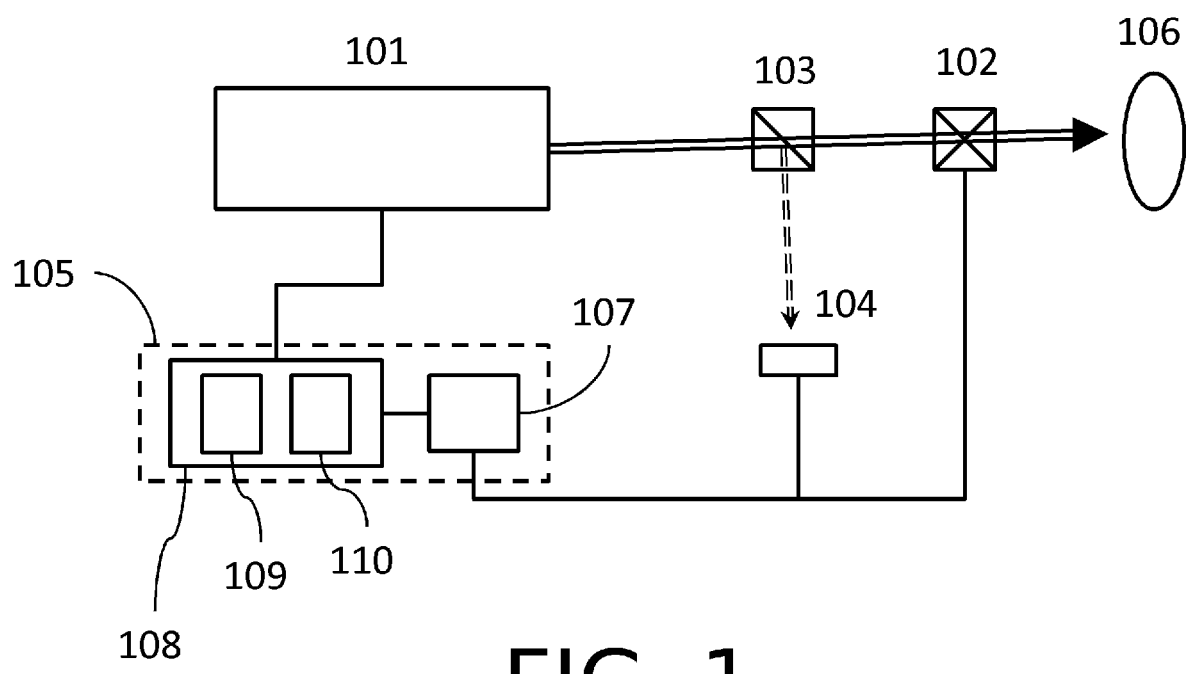
FIG. 1 is a configuration diagram showing an embodiment of a laser apparatus according to the present invention.

FIG. 1 is a configuration diagram showing an example of an embodiment according to the present invention. A laser apparatus has a laser head portion 101 of a lamp excitation solid laser having a flash lamp and a light-shielding device 102 which blocks laser light. The laser apparatus further has a beam splitter 103 disposed on the optical axis of the laser output, a photodetector 104 which detects a laser light flux branched by the beam splitter 103, and a control system 105 which controls the laser apparatus. An irradiated object 106 is a processed product or the like in industrial applications, and is a biometric portion (analyte) in medical applications.

The control system 105 has an external control portion 107 and a laser head control portion 108. In FIG. 1, although the external control portion 107 and the laser head control portion 108 are included in the control system 105, they may be provided independently. In the present invention, although the external control portion 107 is used for controlling the photodetector 104 and the light-shielding device 102, other equipment control mechanisms such as a temperature monitor may be provided.

The laser head control portion 108 has a lamp setting control mechanism 109 for a flash lamp as a major portion of the present invention and a laser control mechanism 110 associated with other laser controls. The laser control mechanism 110 to be mounted is different depending on a lamp excitation solid laser to be used. For example, in a Nd:YAG (neodymium YAG) laser widely used as an industrial processing laser, a Q-switch control portion for forming a high-output pulse light, a shutter control portion installed in a resonator, a temperature control portion which controls the temperatures of a laser medium and the flash lamp, and so on are included. The lamp setting control mechanism 109 includes a repetition frequency control portion, a lamp current control portion which controls a flash lamp emission output, and a simmer current control portion which controls a simmer current (a lamp standby current). The lamp current control is designed to control lamp emission intensity, and lamp voltage control has a function similar to the lamp current control according to a circuit configuration. Therefore, in the present specification, although the lamp current control is described, lamp voltage control as an alternative, is also included within the invention.

Figure 2:
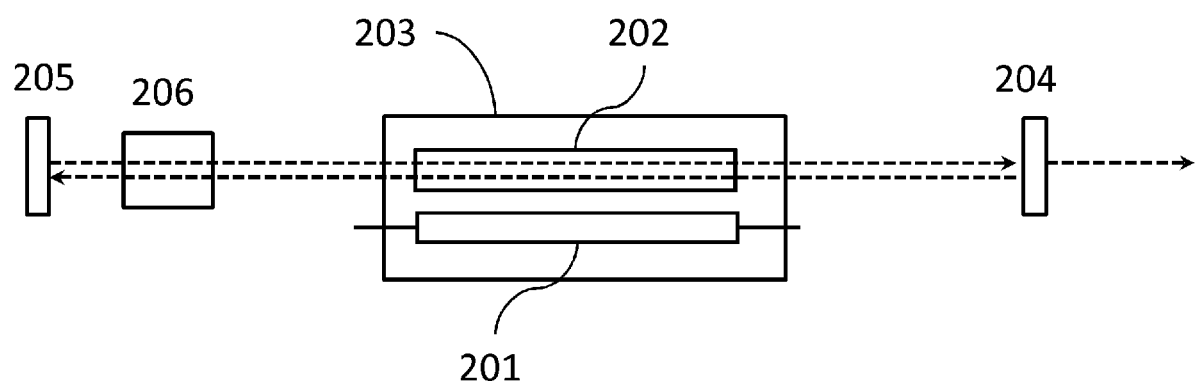
FIG. 2 is a view showing a basic configuration of a laser resonator.

A basic configuration of a resonator structure of the laser head portion 101 is shown in FIG. 2. A flash lamp 201 for excitation source such as xenon and krypton and a laser rod (medium) 202 being a laser medium are arranged at respective focal positions in an elliptical chamber 203. Further, an output mirror 204 and a reflecting mirror 205 constituting the resonator structure are arranged on the axis of the laser rod. A high voltage is applied to the electrodes on the both ends of the flash lamp 201 as an excitation source, and the flash lamp 201 emits light according to the applied electric power. A laser rod 202 disposed on the other side of the chamber 203 is irradiated with the lamp light reflected from the inner surface of the elliptical chamber 203. The laser rod 202 is excited, and a light flux reciprocates between the output mirror 204 and the reflecting mirror 205, so that laser light is oscillated.

In order to enhance the energy output per pulse, a Q-switch 206 using Pockels effect is used. Accumulated energy is instantaneously released, whereby a high energy pulse is produced. By virtue of the high energy of the flash lamp emission and the pulsing of the Q-switch, in the lamp excitation solid laser, laser oscillation with a large pulse energy can be easily obtained. When the Nd:YAG rod is used as the laser medium, a stable high pulse energy can be relatively easily obtained, and it is widely used for industrial application such as processing. However, the laser head portion 101 is not limited to the Nd:YAG laser. There can also be used an alexandrite laser which can enhance the energy output per pulse by the flash lamp excitation, a titanium-sapphire (Ti:sa) laser using second harmonics of Nd:YAG as an excitation source, and so on.

Figure 3:
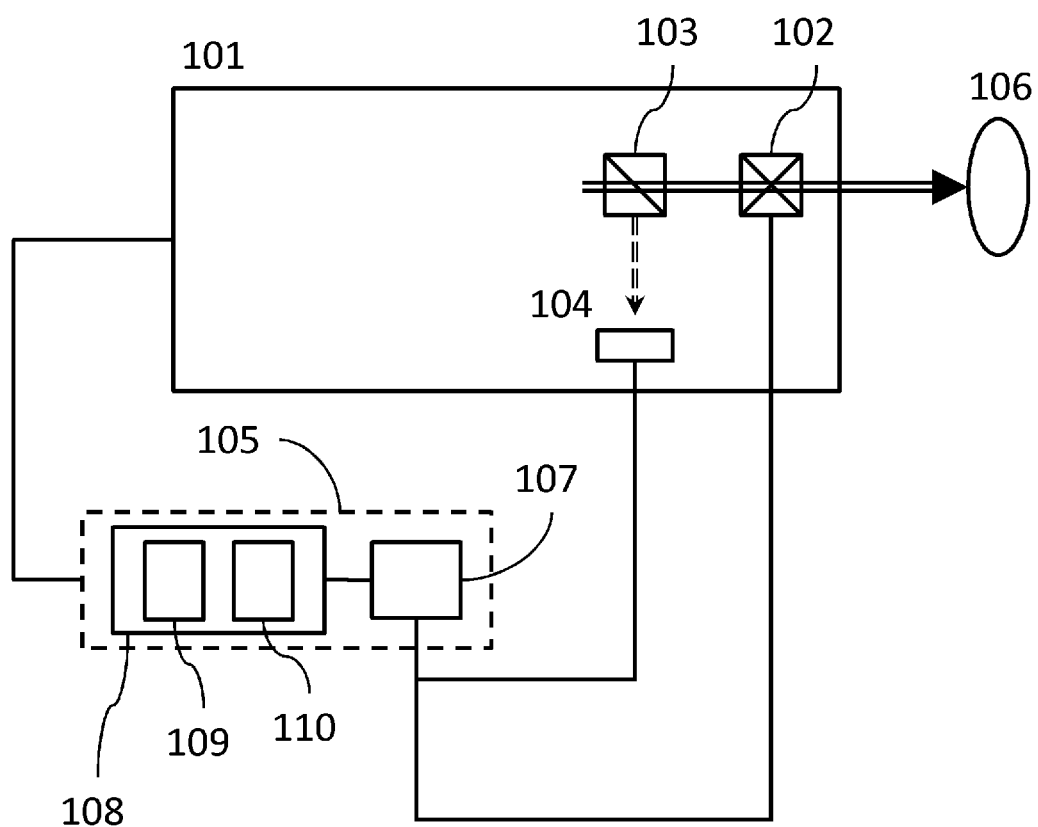
FIG. 3 is a configuration diagram showing an embodiment of the laser apparatus according to the present invention.

The light-shielding device 102 has a termination process portion of laser light. In the termination process portion, the termination process is associated with heat generation due to a high energy of laser light. Thus, it is preferable that the light-shielding device 102 is installed outside a housing of the laser head portion 101, as shown in FIG. 1. However, the light-shielding device 102 may be integrated with the inside of the laser head. When the light-shielding device 102 is integrated with the inside of the laser head, the beam splitter 103 and the photodetector 104 can be similarly integrated with the inside of the laser head. FIG. 3 is a configuration diagram when the laser head portion includes those components.

Output light is measured by sampling a portion of a laser light emitted using the beam splitter 103. Thus, the irradiation intensity for the irradiated object 106 is not significantly reduced, and a laser light may be branched so that the necessary detection sensitivity in the photodetector 104 can be sampled.

A portion of a laser light is measured using the photodetector 104. As the photodetector 104, an energy detector which can mainly measure oscillation pulse energy is suitably used. However, the photodetector is not limited to an energy sensor, and any photodetector may be used as long as it can detect light intensity of CCDs and so on.

Figure 4:
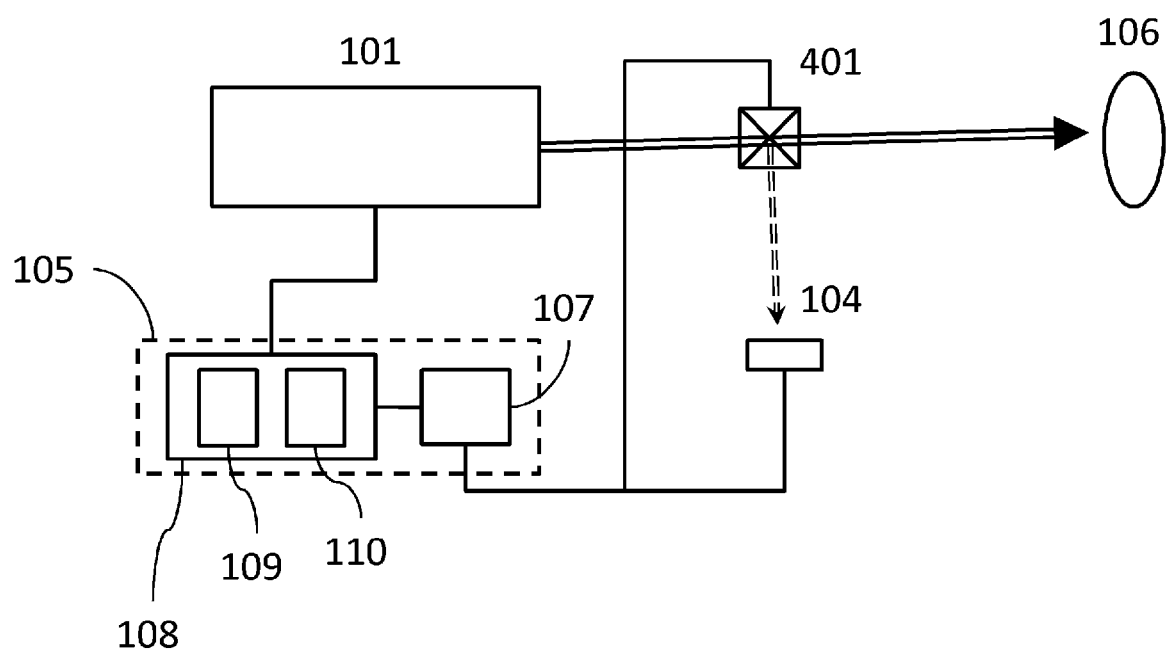
FIG. 4 is a configuration diagram showing an embodiment of the laser apparatus according to the present invention.

In the present invention, the photodetector 104 is installed to measure the laser output at the time when the irradiation to the irradiated object 106 is blocked. When the beam splitter 103 is used, there is an advantage in that an emitted laser light can be continued to be measured constantly. Namely, the reduction of laser output accompanying deterioration of the lamp can be monitored. Note that, the light-shielding device 102 may include the functions of the beam splitter 103 (the light-shielding device may serve as the beam splitter). Such a configuration is shown in FIG. 4. The configuration other than the light-shielding device and the beam splitter is similar to that of FIG. 1. A light-shielding device 401 which blocks laser light is configured not to terminate the laser light directly but takes out at least a portion of a light flux by reflection. The photodetector 104 is installed on an optical path of the partial light flux. According to this constitution, the laser output at the time when the irradiation to the irradiated object 106 is blocked can be measured.

Figure 5:
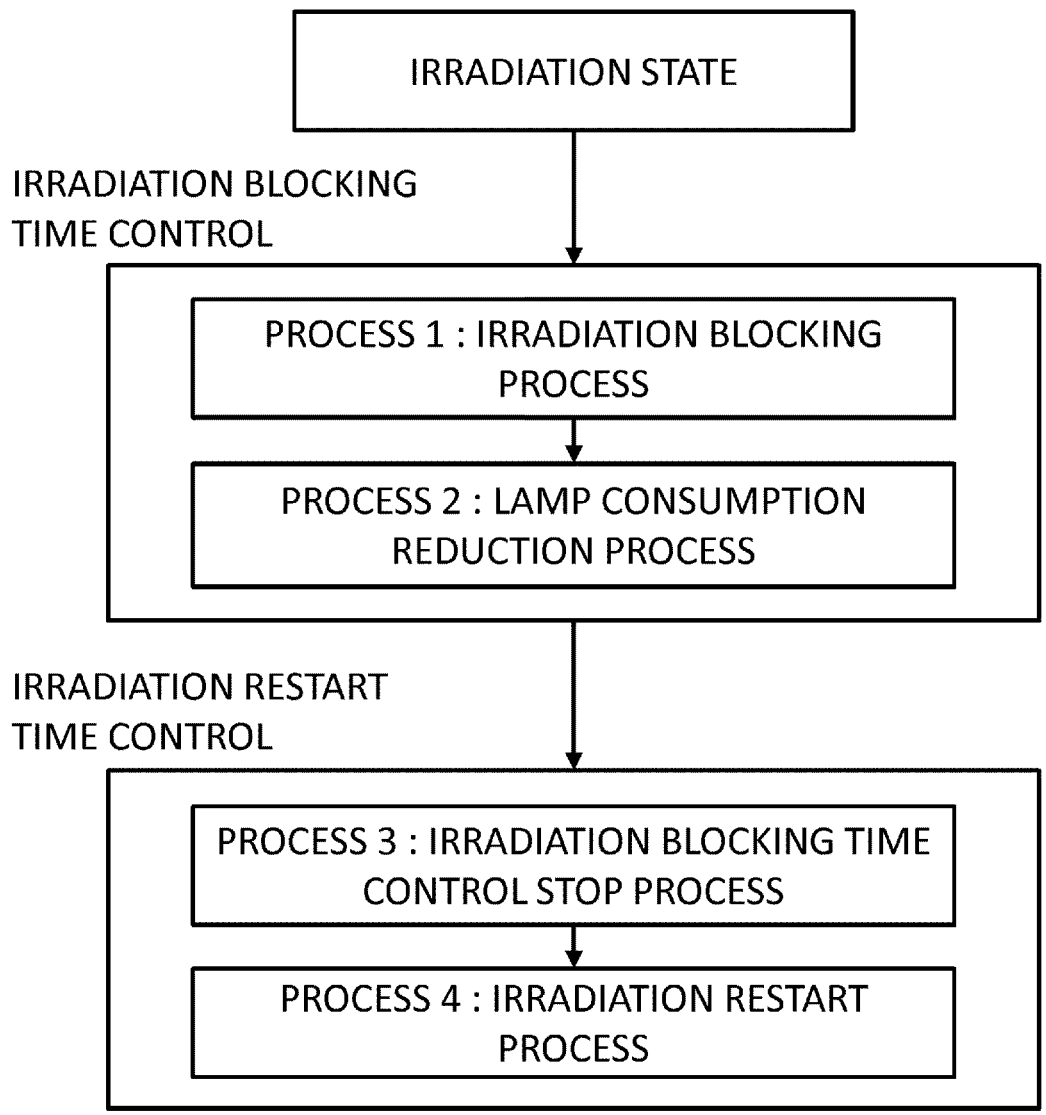
FIG. 5 is a view showing an embodiment of a flow chart of a control method.
Figure 6:
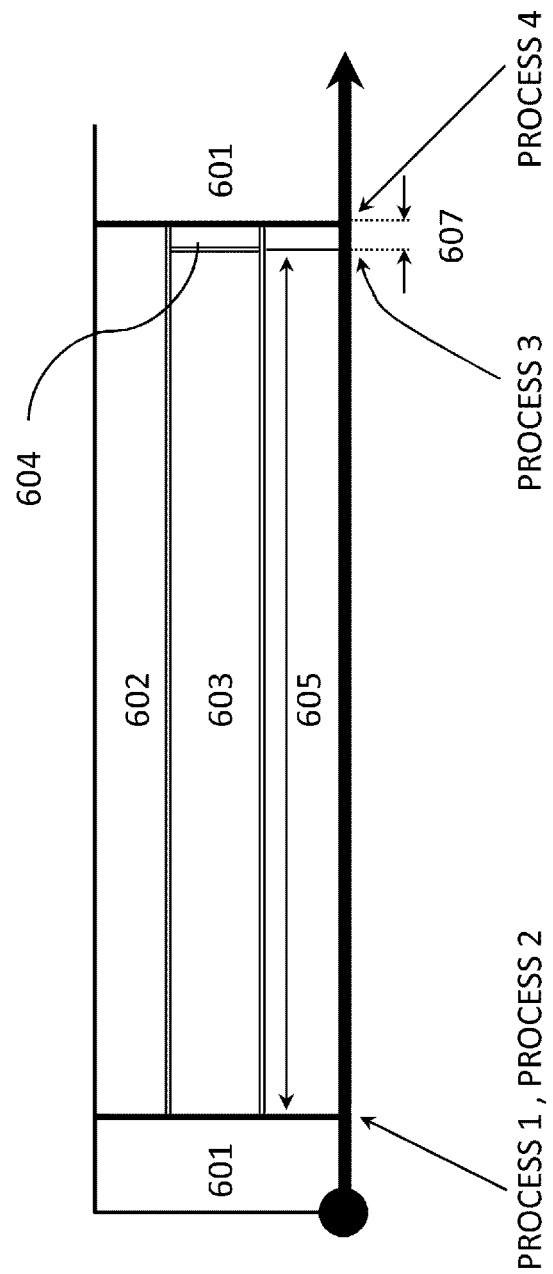
FIG. 6 is a view showing an embodiment of a time chart of the control method and names of intervals between processes.

An example of a method of controlling the laser apparatus as an embodiment of the present invention that can be realized by the configuration of FIGS. 1 to 4 will be described. FIG. 5 shows a flow chart of the control method, and FIG. 6 shows a time chart including a process sequence. FIG. 6 includes an irradiation state 601, a light-shielding state 602, an irradiation/light-shielding time control 603, an irradiation restart time control 604, a consumption reduction period 605, and a waiting period 607.

As shown in FIG. 6, the irradiation/light-shielding time control 603 and the irradiation restart time control 604 are performed during the light-shielding state 602. The irradiation state 601 is a state in which a laser medium is already in the thermal equilibrium state and a stable laser oscillation is obtained. Hereinafter, in this specification, the lamp set state in the irradiation state 601 is referred to as a stable irradiation condition.

In the irradiation/light-shielding time control 603, an irradiation blocking process (process 1 of FIG. 5) and a lamp consumption reduction process (process 2 of FIG. 5) are performed. Processes 1 and 2 are continuously performed to transfer the state from the irradiation state 601 to the light-shielding state 602. The lamp consumption is reduced by process 2.

In the irradiation restart time control 604, an irradiation blocking time control stop process (process 3 of FIG. 5) and an irradiation restart process (process 4 of FIG. 5) are performed. In process 3, a process during the irradiation/light-shielding time control 603 is stopped at any timing, and the process is transferred to the irradiation restart time control 604. The period between process 3 and process 4 is referred to as the waiting period 607.

Although an object of the present invention is to reduce the waiting period 607 and obtain stability of the laser light irradiation, the length of the waiting period 607 is different according to the application. Accordingly, a predetermined waiting time is required to be set according to the application. When the waiting period 607 is relatively long (for example, when a time required from a lamp stop state to a laser rising time is a long time, about the same as the warming-up time), the lamp emission may be stopped simultaneously with the light-shielding state 602.

<Example of Control Method>

Another example of a method of controlling the laser apparatus as an embodiment of the present invention that can be realized by the configuration of FIGS. 1 to 4 will be described. This method can be used as well as the above control method. By virtue of this method, when the consumption of the flash lamp is reduced when irradiation is blocked, it takes time for the laser medium to reach thermal equilibrium when irradiation is restarted, so that it is possible to deal with the phenomenon that it takes time to stabilize the output.

Figure 7:
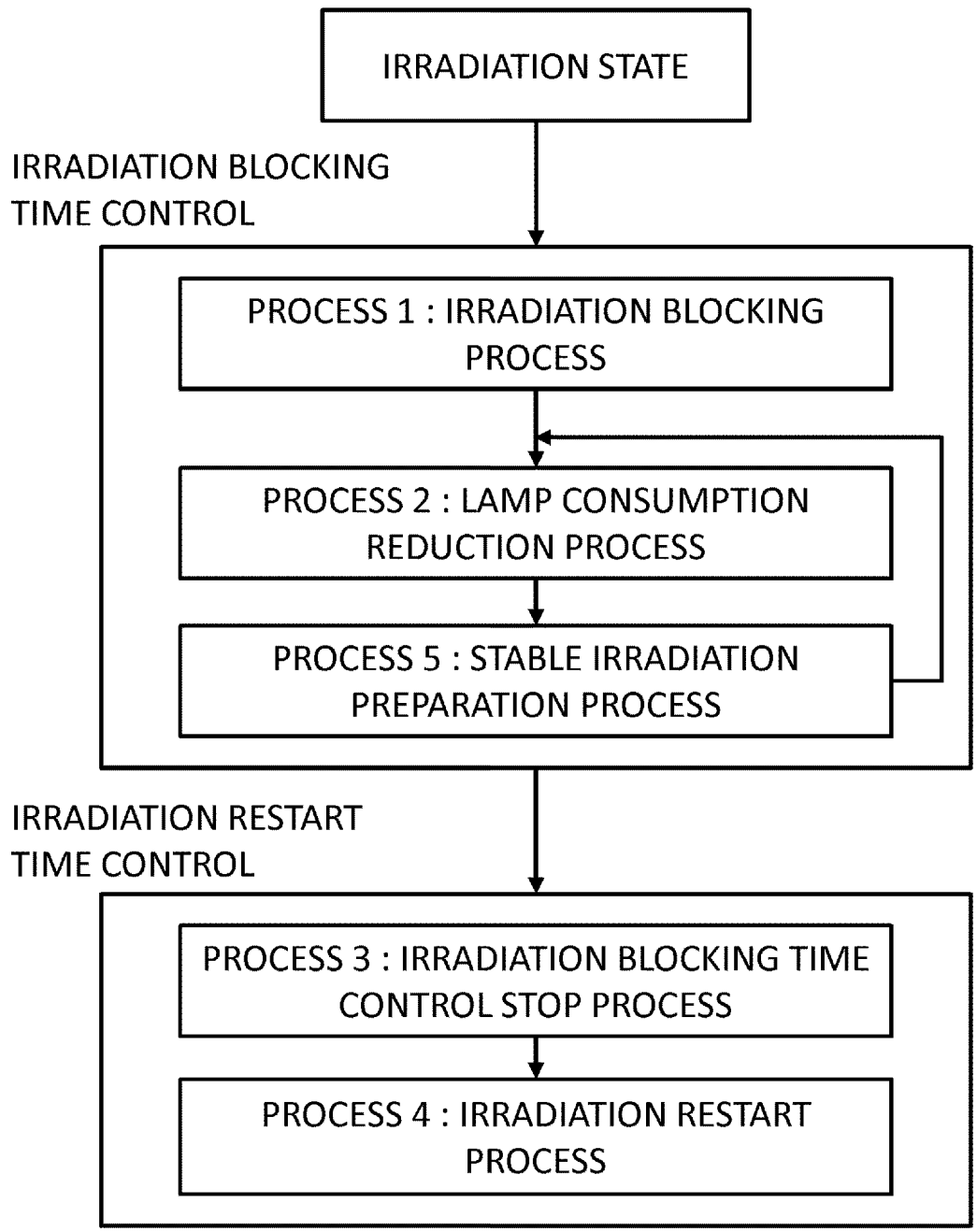
FIG. 7 is a view showing an embodiment of a flow chart of a control method.
Figure 8:
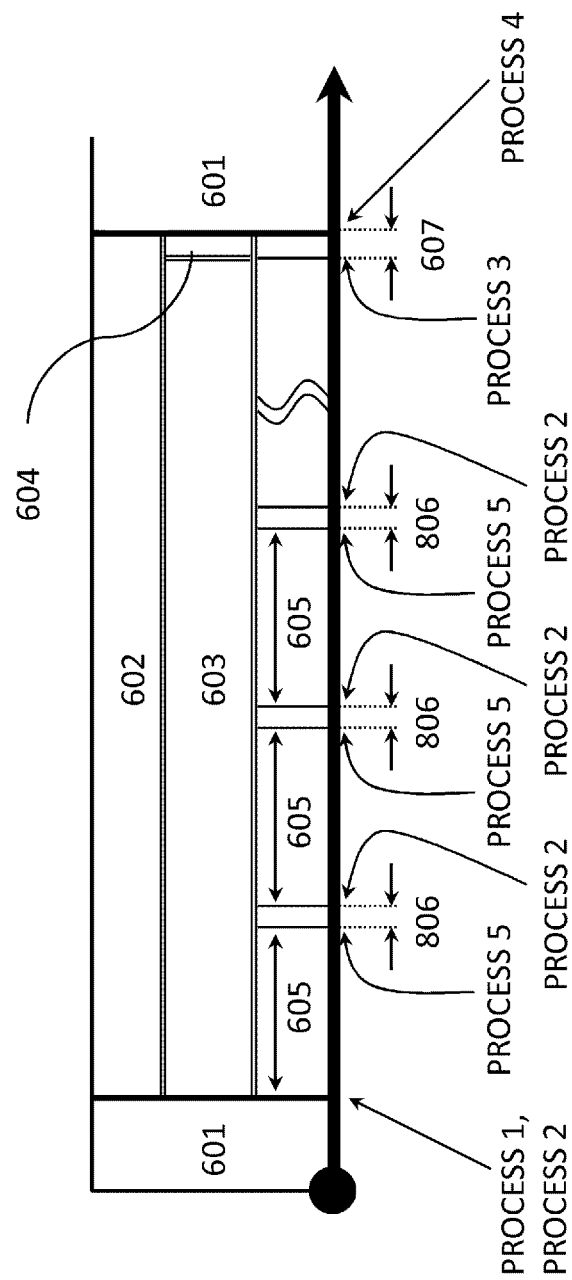
FIG. 8 is a view showing an embodiment of a time chart of the control method and names of intervals between processes.

FIG. 7 shows a flow chart of the control method, and FIG. 8 shows a time chart including a process sequence. FIG. 8 includes the irradiation state 601, the light-shielding state 602, the irradiation/light-shielding time control 603, the irradiation restart time control 604, the consumption reduction period 605, and the waiting period 607 as in FIG. 6 and further includes an irradiation preparation period 806.

As shown in FIG. 7, in the irradiation/light-shielding time control 603, the irradiation blocking process (process 1), the lamp consumption reduction process (process 2), and a stable irradiation preparation process (process 5) are performed. In process 5, the lamp set value is the same as that when the irradiation is restarted, and process 5 is performed for holding a state in which a stable laser oscillation is obtained in a short time when the irradiation is restarted. Process 2 is performed again following the process 5. The period between process 5 and process 2 is referred to as the irradiation preparation period 806. Process 2 and process 5 constitute a loop process, and a state in which the reduction of the lamp consumption and the output stability at the time when irradiation is restarted are simultaneously realized is maintained during the period of the light-shielding state 602. Process 3 and subsequent processing are similar to that in the above control method. The process during the irradiation/light-shielding time control 603 is stopped at any timing in process 3, and the process is transferred to the irradiation restart time control 604. The waiting period 607 may be shorter than the irradiation preparation period 806.

Hereinafter, each process will be described in detail.

In process 1 as the irradiation blocking process, when the apparatus is in the irradiation state 601, the control by the external control portion 107 of the control system 105 is performed at any timing, and irradiation is blocked using the light-shielding device 102. The use of light-shielding components provided inside a laser resonator or the light emission control of the flash lamp stops the laser oscillation, whereby the irradiation may be blocked. However, in the present invention, the irradiation of the irradiated object 106 is blocked while holding the laser oscillation state in the above constitution.

Following process 1, in process 2 as the lamp consumption reduction process (consumption reduction start process), the lamp set value is changed by the lamp setting control mechanism 109 of the control system 105. In order to reduce the lamp consumption, the setting conditions of the repetition frequency control portion, the lamp current control portion, and the simmer current control portion are changed by a lamp setting control. The setting conditions will be described in detail later.

In process 3 as the process of stopping the irradiation blocking time control (consumption reduction stop process), the lamp set value changed for the reduction of the lamp consumption in process 2 is changed to a lamp setting value for re-irradiation of the irradiated object 106. The lamp setting at the time of re-irradiation may be the same as or different from the lamp setting at the time of initial irradiation. When a cycle to the re-irradiation from process 1 to process 4 is one cycle, the lamp setting value at the time of irradiation may be changed in each cycle.

The lamp setting value will be described as follows.

In the lamp setting value, the reduction of the repetition frequency significantly contributes to the reduction of the lamp consumption. For example, in a Nd:YAG laser with a repetition frequency of 10 to 20 Hz and an energy output per pulse of 1 J, although depending on the internal constitution of a laser head and lamp setting conditions at the time of irradiation, the life of the lamp is approximately ten million shots. The flash lamp has an individual specificity in the length of its life, and at times the life is approximately several million shots even in the lamp having the same specification. Thus, the reduction of the repetition frequency is effective for the reduction of lamp consumption. For example, in a Nd:YAG laser with a repetition frequency of 20 Hz in the stable irradiation conditions, the set frequency can be selected from 5 Hz, 1 Hz, and so on, and the lower the repetition frequency that is set, the higher the effect of reducing the lamp consumption.

However, when the repetition frequency of the lamp setting value is reduced, the lamp emission irradiation amount per time for the laser medium is reduced, and therefore, the thermal equilibrium state of the laser medium is collapsed. Consequently, the thermal lens effect is changed, and the state of the resonator is changed from the optimum state; therefore, the laser output is gradually attenuated. An object of the present invention is to obtain immediate stabilization of the energy output of the laser oscillation at the time of irradiation. To achieve this object, the irradiation preparation period 806 (and the waiting period 607) is required to be shortened. The time required for the irradiation preparation period 806 (and the waiting period 607) is different depending on the state of the laser medium, and namely the length of the consumption reduction period 605 is different depending on the length of the irradiation preparation period 806 being set.

Figure 9:
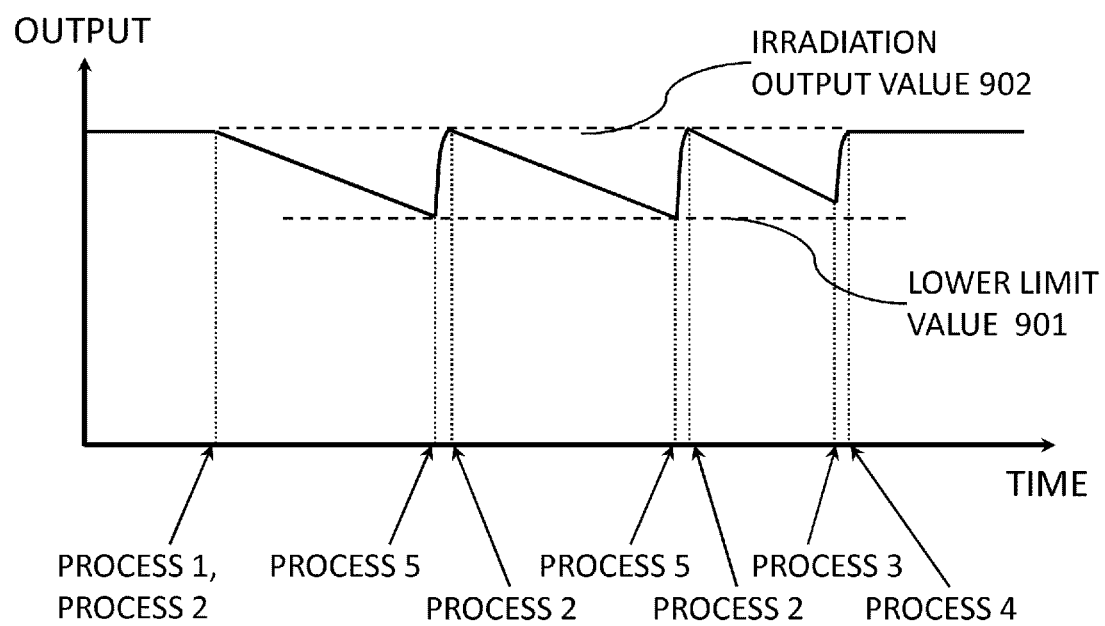
FIG. 9 is a view showing a laser output for a control process.

The length of the consumption reduction period 605 can be determined by measurement of the change of the laser oscillation output. For example, when the repetition frequency in process 2 is set to 1 Hz, the laser medium is gradually cooled, and the laser oscillation output is reduced. The condition capable of obtaining the irradiation preparation period 806 that is desired is that the laser medium is not excessively cooled and the irradiation condition can be immediately returned to the stable irradiation condition in process 5. In FIG. 9, the horizontal axis is time, and the vertical axis is the laser output. The laser output value that can return the irradiation state to the stable irradiation state within a time period of the irradiation preparation period 806 being desired is a lower limit value 901. The time for reaching the lower limit value 901 is the length of the consumption reduction period 605. When the repetition frequency set in process 2 is close to the repetition frequency in the stable irradiation condition, it is assumed that the energy output value in the thermal equilibrium state is larger than the lower limit value 901. The present invention includes such a condition. However, when the lamp consumption reduction effect is considered, it is effective and preferable that the repetition frequency is set lower in process 2.

In the lamp setting value, the reduction of the lamp current value can reduce a lamp load associated with light emission and reduce the lamp consumption. As with the lamp repetition frequency, the lamp current value is reduced in process 2, and the lamp current value becomes the value at the time of the re-irradiation in processes 3 and 5, whereby output stability at the time of irradiation and reduction of the lamp consumption can be realized. When the lamp current is reduced in process 2, the length of the consumption reduction period 605 is different depending on the lamp current setting value as with the reduction of the repetition frequency. The lower limit value of the lamp current is a current threshold value that excites the laser medium to enable the laser oscillation. When the lamp setting current value in the consumption reduction period 605 is near a threshold value, the lamp current value is very low and the oscillation output is very small, and therefore, the lamp consumption reduction effect is large. However, since the heat absorption amount of the laser medium is reduced, the thermal equilibrium state of the flash lamp is significantly changed. Thus, when the laser light irradiation to the irradiated object 106 is restarted, the consumption reduction period 605 is required to be reduced in order to obtain a stable energy output in a short time. Further, since the excitation state of the laser medium is unstable, an energy value detected when the irradiation is blocked may be unstable. Although a certain effect can be obtained even in the setting of the lamp current value near the lower limit value, preferred is a lamp current value that stabilizes the measured energy value in the photodetector 104 and stabilizes the excitation state of the laser medium.

In process 2, although at least the lamp repetition frequency or the lamp current value is reduced, both the lamp setting controls may be performed at the same time.

In the lamp setting values, the simmer current is a standby current previously energized to the flash lamp before the lamp emission for stable laser oscillation purposes. As the simmer current is reduced, the load on the lamp is reduced, also reducing the lamp consumption; however, the simmer current value is optimized according to the lamp current value and the repetition frequency as the stable irradiation conditions. Thus, simultaneously with the reduction of the lamp repetition frequency or the lamp current, the simmer current is reduced in process 2, and the simmer current at the time of the re-irradiation is applied in processes 3 and 5, whereby the output stability at the time of the irradiation and the reduction of the lamp consumption can be realized.

The process transitions from process 3 to process 4, from process 2 to process 5, and from process 5 to process 2 can be automatically performed by two control sequences to be described later. One of the control sequences is referred to as an output control sequence, and the other is referred to as a time control sequence.

When the process is transferred from process 2 to process 5, in the output control sequence, a value measured by the photodetector 104 is input to the external control portion 107 of the control system 105, and when a value not more than a predetermined lower limit value is input, the process is transferred to process 5. In the time control sequence, the consumption reduction period 605 is previously measured using the photodetector 104, and the time is set. In the actual measurement, the process is transferred to process 3 in accordance with the set time in the control system 105.

When the process is transferred from process 5 to process 2 again, as in the transition from process 2 to process 5, the output control sequence and the time control sequence can be performed. In the output control sequence, as shown in FIG. 9, the time for reaching an irradiation output value 902 in the stable irradiation condition is the irradiation preparation period 806 (shown in FIG. 8). The laser output is detected by the photodetector 104, and the detected value is input to the control system 105 to be compared with the irradiation output value 902, so that the process can be automatically transferred to process 2. For example, when a detected value of an output is not less than the irradiation output value, the process may be transferred to process 2.

When the transition from process 5 to process 2 is performed by the time control sequence, the following procedure is used. After process 5, the irradiation preparation period 806 for reaching the irradiation output value 902 is previously measured, and after a lapse of the irradiation preparation period 806, the process is transferred to process 2 again by the control system 105. At this time, stability after the restart of irradiation may be lost depending on the device and measurement conditions. For example, when the irradiation preparation period 806 is very short, stability may be lost. In this case, the stability after the restart of irradiation can be obtained by using the output control sequence in which the output of the photodetector is referred, and thus the output control sequence is preferred. Meanwhile, in terms of the fact that the reduction of the irradiation preparation period 806 (and the waiting period 607) is one object of the present invention, it is preferable to make a determination in advance of the irradiation preparation period 806 according to the use conditions. Accordingly, as long as the condition that the output stability is obtained after the restart of irradiation is met, the time control sequence is more preferable.

Process 2 and process 5 are sequentially repeated, whereby the desires to obtain the output stability at the time of laser light irradiation and flash lamp consumption reduction at the time of laser blocking can be satisfied at the same time.

A case where the output control sequence is used in the transition from process 3 to process 4 is similar to the case where the process is transferred from process 5 to process 2 again. Since process 3 is performed at any timing, the length of the waiting period 607 is not more than the length of the irradiation preparation period 806. Thus, when the time control sequence is used, the length of the waiting period 607 is the same as the length of the irradiation preparation period 806. Consequently, regardless of the timing of performing process 3, the stable irradiation state can be maintained when the process is transferred to process 4.

<Example of Apparatus>

Figure 10:
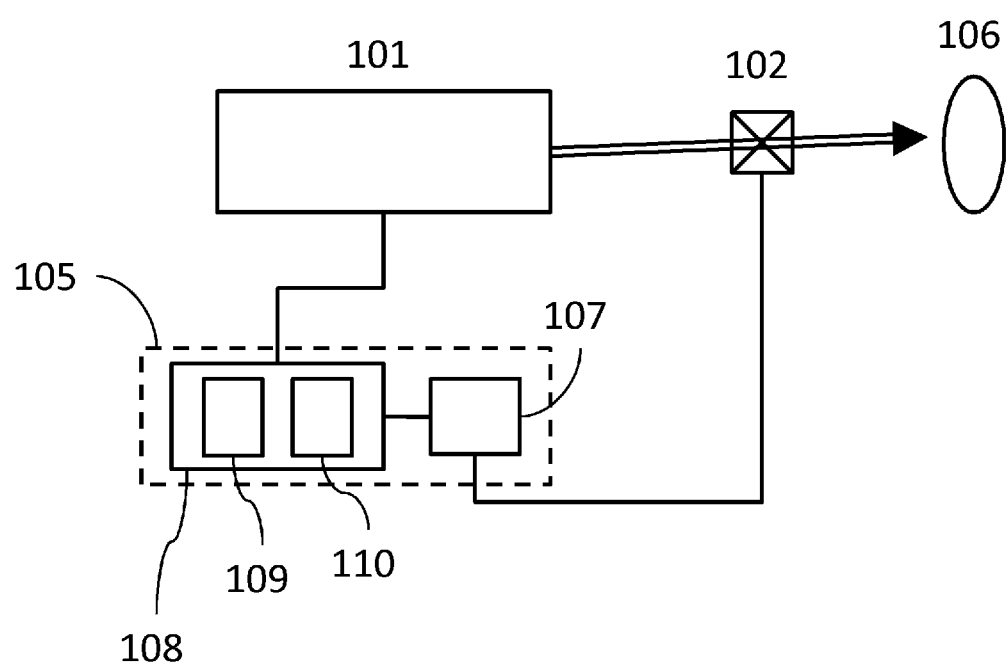
FIG. 10 is a configuration diagram showing an embodiment of a laser apparatus of the present invention.

FIG. 10 is a configuration diagram showing an example of an embodiment of the present invention. A laser apparatus is constituted of the laser head portion 101 of a lamp excitation solid laser, the light-shielding device 102 blocking a laser light, and the control system 105 performing the laser apparatus control. The irradiated object 106 is a processed product and so on in industrial application and is a biometric portion in medical application. Unlike the embodiment shown in FIGS. 1 and 4, the beam splitter 103 and the photodetector 104 are not included. In the method of controlling the laser apparatus according to the present embodiment, the time control sequence is used. Namely, the output in the light-shielding state is measured by the photodetector 104 before utilization of the laser apparatus, and the time control sequence is determined. The control process is similar to that in the case of using the laser apparatus of FIG. 1.

Example 1

Hereinafter, an example of the method of controlling the laser apparatus used in a photoacoustic measurement apparatus for medical diagnosis is shown. The laser apparatus configured in FIG. 1 is used. This laser apparatus is constituted of the laser head portion 101, the light-shielding device 102 blocking a laser light, the beam splitter 103, the photodetector 104, and the control system 105 controlling the laser apparatus.

The laser head portion 101 is constituted of an Nd:YAG laser and a titanium-sapphire (Ti:sa) laser using second harmonics of the Nd:YAG laser as an excitation source. A breast phantom (this is a known pseudo-living body element) is used as the irradiated object 106. As the stable irradiation condition in the irradiation state 601, the lamp repetition frequency is 20 Hz, and the lamp current value that obtains the energy output of 100 mJ/pulse at a wavelength of 800 nm is used. In order to obtain a large pulse energy as an emission energy, a flash lamp is used as an excitation source of the Nd:YAG laser. Each pulse light intensity is measured using a pyroelectric sensor as the photodetector 104. The control system 105 is constituted of the external control portion 107 and the laser control portion 108.

Four measurements are continued by the following process. In the first measurement, a left breast phantom CC direction is measured. In the second measurement, a left breast phantom MLO direction is measured. In the third measurement, a right breast phantom CC direction is measured. In the fourth measurement, a right breast phantom MLO direction is measured. Although fixation of the breast phantom can be easily changed, it is assumed that the time of approximately 4 minutes are required in actual clinical practice and thus the measurement interval is 4 minutes. The measurement sequence is previously determined before the breast phantom measurement. The lamp repetition frequency at the time of light shielding is 1 Hz, and the irradiation preparation period 806 is 5 seconds. When the consumption reduction period is measured so that the irradiation preparation period 806 is 5 seconds, the consumption reduction period is 180 seconds. While the irradiation output value 902 in the stable irradiation condition is 4 mJ/pulse, the lower limit value 901 of the laser output determining the consumption reduction period 605 is 2 mJ/pulse. The waiting period 607 in the irradiation restart time control 604 is 5 seconds, as in the irradiation preparation period 806.

Figure 11:
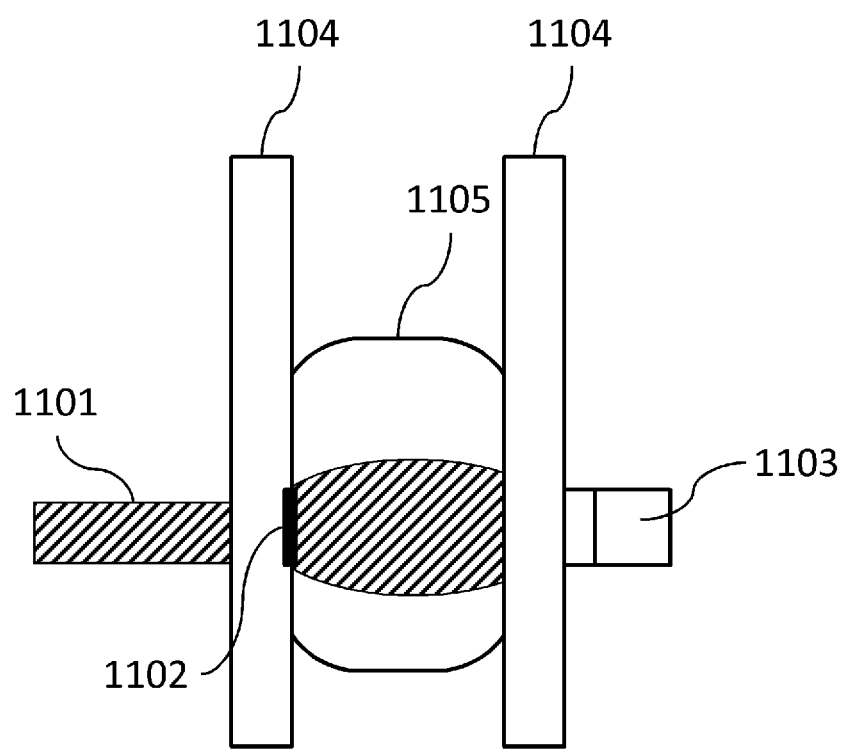
FIG. 11 is a top view of a photoacoustic measurement apparatus.

FIG. 11 is a top view of the photoacoustic measurement apparatus for medical diagnosis used in the measurement. A laser light flux 1101 is applied to a breast phantom 1105 through a transparent pressing-fixing parallel plate 1104. The laser light flux emitted from the laser apparatus shown in FIG. 1 is expanded, and the shape is formed, so that the laser light flux 1101 with which a desired irradiation region 1102 is irradiated, is obtained. An ultrasound probe 1103 is disposed on the opposing side of the laser light irradiation region 1102 through the breast phantom 1105 and the pressing-fixing parallel plate 1104, and a photoacoustic signal generated by the laser light irradiation is detected.

First, laser light having a stable energy output is irradiated to be applied to a breast in the stable irradiation condition, and the first measurement is performed. The measurement time is 1 minute.

Then, after the termination of the measurement, the irradiation blocking process (process 1) is performed. The irradiation is blocked by the light-shielding device 102 in accordance with the control from the external control portion 107 of the control system 105. The energy output after process 1 is 4 mJ.

The lamp consumption reduction process (process 2) is performed following process 1. In this process, the lamp repetition frequency is reduced to 1 Hz using the lamp setting control mechanism 109 of the control system 105.

Then, the process is transferred from process 2 to process 5 using the output control sequence. The output value measured by the photodetector 104 is input to the external control portion 107, and when the output energy reaches 2 mJ/pulse as the predetermined lower limit value 901, the process is transferred to the stable irradiation preparation process (process 5). The consumption reduction period 605 is 190 seconds. In process 5, the repetition frequency is returned to 20 Hz as the stable irradiation condition, using the lamp setting control mechanism 109.

In the transition from process 5 to process 2, the time control sequence is used. In the external control portion 107, the process 2 is performed again after a lapse of 5 seconds from the execution of process 5. The repetition frequency at this time is 1 Hz.

After a lapse of 4 minutes from the termination of the first measurement, the second measurement is performed. In order to perform the second measurement, the irradiation blocking time control stop process (process 3) is performed. The repetition frequency is set to 20 Hz as the stable irradiation condition in the irradiation state, using the lamp setting control mechanism 109.

In the transition from process 3 to process 4, the time control sequence is used. After a lapse of 5 seconds from the execution of process 3, the second measurement is started by process 4 of releasing the light-shielding state using the light-shielding device 102 through the external control portion 107. The value of the photodetector 104 is 4 mJ/pulse from the start of the second measurement.

Subsequently, the above measurement process is repeated four times. After the termination of the measurement, the lamp emission is immediately stopped.

The actual number of times of lamp emission in this process will be considered. The irradiation state 601 which is the time of measuring the breast phantom is 4 minutes, and the repetition frequency is 20 Hz; therefore, the number of times of lamp emission is 4800 shots. The total time of the light-shielding state 602 is 12 minutes because the measurement interval is 4 minutes. During this period, the total period of time during which the repletion frequency is 20 Hz is 20 seconds, because the period of time during which the repletion frequency is 20 Hz is 15 seconds in the irradiation preparation period 806 between the process 3 and the process 2 and 5 seconds in the waiting period 607 between the process 4 and the process 5. The number of times of lamp emission during this period is 400 shots. Meanwhile, the consumption reduction period 605 is 11 minutes 40 seconds, and the repetition frequency during this period is 1 Hz. Thus, the number of times of lamp emission during this period is 700 shots. That is, the lamp emission of 1100 shots is performed in all in the light-shielding state. The lamp emission of 5,900 shots is performed in all in this measurement process.

Meanwhile, the number of times of lamp emission in the case of not using the control method in this process will be considered. The entire measurement time in this process is 16 minutes, and if the repetition frequency during this period is maintained at 20 Hz, the number of times of lamp emission is 19,200 shots. When it is considered that the lamp consumption is simply proportional to the number of times of lamp emission, three or more times the consumption reduction effect will tend to be obtained. Meanwhile, when the measurement is restarted, a stable output is obtained in 5 seconds at all times. Thus, it is found that by virtue of the use of the measurement control method, the output stability and the lamp consumption reduction are satisfied at the same time.

Example 2

Hereinafter, an example of the method of controlling the laser apparatus used in a photoacoustic measurement apparatus for medical diagnosis is shown. The laser apparatus configured in FIG. 1 is used. This laser apparatus is constituted of the laser head portion 101, the light-shielding device 102 blocking a laser light, the beam splitter 103, the photodetector 104, and the control system 105 controlling the laser apparatus.

An alexandrite laser is used in the laser head portion 101. A breast phantom being a pseudo living body is used as the irradiated object 106. As the stable irradiation condition in the irradiation state 601, the lamp repetition frequency is 20 Hz, and the lamp current value for obtaining the energy output of 100 mJ/pulse at a wavelength of 750 nm is 100 A. In order to obtain a large pulse energy as an emission energy, a flash lamp is used as an excitation source of the alexandrite laser. Each pulse light intensity is measured using a pyroelectric sensor as the photodetector 104. The control system 105 is constituted of the external control portion 107 and the laser control portion 108.

Four measurements are continued by the following process. In the first measurement, a left breast phantom CC direction is measured. In the second measurement, a left breast phantom MLO direction is measured. In the third measurement, a right breast phantom CC direction is measured. In the fourth measurement, a right breast phantom MLO direction is measured. Although fixation of the breast phantom can be easily changed, it is assumed that the time of approximately 4 minutes are required in actual clinical practice and thus the measurement interval is 4 minutes. The measurement sequence is previously determined before the breast phantom measurement. The lamp current value at the time of light shielding is 70 A, and the irradiation preparation period 806 is 5 seconds. When the consumption reduction period is measured so that the irradiation preparation period 806 is 5 seconds, the consumption reduction period is 130 seconds. While the irradiation output value 902 in the stable irradiation condition is 5 mJ/pulse, the lower limit value 901 of the laser output determining the consumption reduction period 605 is 2 mJ/pulse. The waiting period 607 in the irradiation restart time control 604 is 5 seconds, as in the irradiation preparation period 806.

FIG. 11 is a top view of the photoacoustic measurement apparatus for medical diagnosis used in the measurement. A laser light flux 1101 is irradiated to a breast phantom 1105 through a transparent pressing-fixing parallel plate 1104. The laser light flux emitted from the laser apparatus shown in FIG. 1 is expanded, and the shape is formed, so that the laser light flux 1101 irradiated to a desired irradiation region 1102 is obtained. An ultrasound probe 1103 is disposed on the opposing side of the laser light irradiation region 1102 through the breast phantom 1105 and the pressing-fixing parallel plate 1104, and a photoacoustic signal generated by the laser light irradiation is detected.

A laser light having a stable energy output is irradiated to a breast in the stable irradiation condition, and the first measurement is performed. The measurement time is 1 minute.

After the termination of the measurement, the irradiation blocking process (process 1) is performed. The irradiation is blocked by the light-shielding device 102 in accordance with the control from the external control portion 107 of the control system 105. The energy output after process 1 is 5 mJ.

The lamp consumption reduction process (process 2) is performed following process 1. In this process, the lamp current value is reduced to 70 A using the lamp setting control mechanism 109 of the control system 105.

In the transition from process 2 to process 5, the output control sequence is used. The output value measured by the photodetector 104 is input to the external control portion 107, and when the output value reaches 2 mJ/pulse as the predetermined lower limit value 901, the process is transferred to the stable irradiation preparation process (process 5). The consumption reduction period 605 is 135 seconds.

In process 5, the lamp current value is returned to 100 A as the stable irradiation condition, using the lamp setting control mechanism 109. In the transition from process 5 to process 2, the time control sequence is used. In the external control portion 107, the process is transferred to process 2 again after a lapse of 5 seconds from the process 5. The lamp current value at this time is 70 A.

After a lapse of 4 minutes from the termination of the first measurement, the second measurement is performed. In order to perform the second measurement, the irradiation blocking time control stop process (process 3) is performed. The lamp current value is set to 100 A as the stable irradiation condition, using the lamp setting control mechanism 109.

In the transition from process 3 to process 4, the time control sequence is used. After a lapse of 5 seconds from the execution of process 3, the second measurement is started by the process 4 of releasing the light-shielding state using the light-shielding device 102 through the external control portion 107. The value of the photodetector 104 is 5 mJ/pulse from the start of the second measurement.

The above measurement process is repeated to perform the measurement four times. After the termination of the measurement, the lamp emission is immediately stopped.

In order to estimate the lamp consumption reduction effect in this measurement, the following experiment is performed.

Four flash lamps A, B, C, and D in which the output pulse energy is 100 mJ/pulse when the lamp current was 100 A are selected. Flash lamps A and B continue laser oscillation for 40 hours at a lamp current of 100 A and a repetition frequency of 20 Hz. Meanwhile, flash lamps C and D continue laser oscillation for 40 hours at a lamp current of 70 A and a repetition frequency of 20 Hz. After that, the energy output is measured at a lamp current of 100 A and a repetition frequency of 20 Hz, using flash lamps A, B, C, and D.

As a result, the energy outputs in the case of using flash lamps A, B, C, and D are 84 mJ/pulse, 82 mJ/pulse, 89 mJ/pulse, and 91 mJ/pulse, respectively. Although there is an individual difference depending on a flash lamp, differences occur in the output energy indicating the lamp consumption according to the lamp current in use. It is found that compared with flash lamps A and B, the lamp consumption reduction effect is large in flash lamp C and D operated at low current.

According to the above results, it is found that the lamp consumption can be reduced by using the lamp current control in example 2. Meanwhile, when the measurement is restarted, a stable output can be obtained in 5 seconds at all times. Thus, it is found that the control method in example 2 satisfies the output stability at the time of irradiation and the lamp consumption reduction at the time of light shielding at the same time.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2011-136236, filed on Jun. 20, 2011, which is hereby incorporated by reference herein its entirety.

What is claimed is:

1. A laser apparatus comprising:
a laser medium;
a resonator including mirrors, with said laser medium interposed between said mirrors;
an excitation unit configured to irradiate said laser medium with excitation light for exciting said laser medium;
a beam splitter disposed outside said resonator and configured to split laser light emitted from said resonator;
a light detector disposed outside the resonator and configured to detect a portion of the laser light split by said beam splitter;
a light-shielding unit disposed outside said resonator and arranged to block another portion of the laser light, wherein the portion of the laser light being a portion that has been split off by the beam splitter and is not detected by said light detector; and a control unit configured to select a light irradiation state, and a light-shielding state in which said light-shielding unit is arranged to block more of the laser light emitted from said resonator as compared with the light irradiation state, wherein, in the light-shielding state, said excitation unit irradiates the excitation light so as to reduce consumption of said excitation unit as compared with the light irradiation state under control of a setting value, and wherein said control unit is configured to control the setting value based on an output from said light detector in the light shielding state.

2. The laser apparatus of claim 1, wherein said control unit is configured to control the setting value such that the output from said light detector is within a predetermined range, in the light shielding state.

3. The laser apparatus of claim 1, wherein the setting value is a value of simmer current for said excitation unit.

4. The laser apparatus of claim 3, wherein said control unit is configured to increase the value of simmer current for said excitation unit when the output from said light detector is equal to or less than a predetermined threshold, in the light shielding state.

5. The laser apparatus of claim 3, wherein said control unit is configured to reduce the value of simmer current when the output from said light detector is equal to or more than a predetermined threshold, in the light shielding state.

6. The laser apparatus of claim 4, wherein the predetermined threshold is a value that enables achievement of the light irradiation state within a predetermined time period.

7. The laser apparatus of claim 6, wherein the predetermined time period is equal to or less than 5 seconds.

8. A photoacoustic apparatus comprising:
the laser apparatus of claim 1, and
a probe configured to detect an acoustic wave in an object generated by irradiation of light emitted from said laser apparatus.

9. The laser apparatus of claim 5, wherein the predetermined threshold is a setting value set for said excitation unit in the light irradiation state.

10. The laser apparatus of claim 2, wherein said control unit is configured to control the setting value so that the output from said light detector is equal to or more than a predetermined threshold, in the light shielding state.

11. The laser apparatus of claim 10, wherein the predetermined threshold is a value that enables achievement of the light irradiation state within a predetermined time period.

12. The laser apparatus of claim 11, wherein the predetermined time period is equal to or less than 5 seconds.

13. The laser apparatus of claim 2, wherein said control unit is configured to control the setting value so that the output from said light detector is equal to or less than a predetermined threshold, in the light shielding state.

14. The laser apparatus of claim 13, wherein the predetermined threshold is a setting value set for said excitation unit in the light irradiation state.

* * * * *